United States Patent [19]

Meyer et al.

[11] 4,163,792
[45] Aug. 7, 1979

[54] INSECTICIDAL OXADIAZOLE ESTERS

[75] Inventors: Willy Meyer, Riehen; Jozef Drabek, Oberwil; Laurenz Gsell, Füllinsdorf; Friedrich Karrer, Zofingen, all of Switzerland

[73] Assignee: Ciba-Geigy Corporation, Ardsley, N.Y.

[21] Appl. No.: 849,744

[22] Filed: Nov. 9, 1977

Related U.S. Application Data

[63] Continuation-in-part of Ser. No. 684,691, May 10, 1976, abandoned.

[30] Foreign Application Priority Data

May 13, 1975 [CH] Switzerland .......................... 6157/75
Apr. 6, 1976 [CH] Switzerland .......................... 4300/76

[51] Int. Cl.$^2$ .......................... A01N 9/22; A01N 9/28; C07D 271/06
[52] U.S. Cl. .............................. 424/272; 260/307 G
[58] Field of Search ................... 260/307 G; 424/272

[56] References Cited

U.S. PATENT DOCUMENTS 3,879,407  4/1975  Hagarty ........................ 260/302 D

FOREIGN PATENT DOCUMENTS 841727 11/1976 Belgium .

OTHER PUBLICATIONS

Burt et al.,–Pestic. Sci. 1974, 5, 791–799.

Primary Examiner—Raymond V. Rush
Attorney, Agent, or Firm—Harry Falber

[57] ABSTRACT 2,2-Dimethyl-3-vinyl-cyclopropanecarboxylic acid esters of the formula

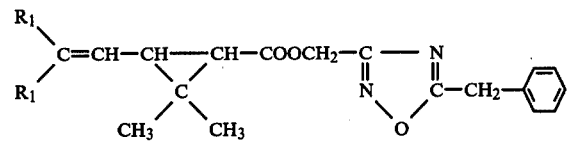

wherein $R_1$ represents fluorine, chlorine or bromine, processes for their production and their use in pest control.

7 Claims, No Drawings

INSECTICIDAL OXADIAZOLE ESTERS

This is a continuation-in-part application of the parent application Ser. No. 684,691, filed May 10, 1976, now abandoned.

The present invention relates to 2,2-dimethyl-3-vinyl-cyclopropanecarboxylic acid esters, to processes for their production and to their use in pest control. The 2,2-dimethyl-3-vinyl-cyclopropanecarboxylic acid esters have the formula $$\begin{array}{c} R_1 \\ \phantom{R}\diagdown \\ \phantom{RR}C=CH-CH-CH-COO-CH_2-C\!=\!\!=\!\!N \\ \phantom{R}\diagup \phantom{RRRRR} \diagdown / \phantom{RRRRRRRRR} \| \phantom{R} \| \\ R_1 \phantom{RRRRRRRR} C \phantom{RRRRRRRRRRR} N \phantom{RR} C-CH_2-\!\!\bigcirc \\ \phantom{RRRRRRRRR} / \diagdown \phantom{RRRRRRRRRRRRR} \diagdown \diagup \\ \phantom{RRRRRRR} CH_3 \phantom{R} CH_3 \phantom{RRRRRRRRRRRR} O \end{array} \quad (I)$$

wherein $R_1$ represents fluorine, chlorine or bromine. The compounds of formula I can be produced by methods known per se; for example they can be produced as follows:

(1)
$$R_1\text{-substituted acid (II)} + Z-CH_2-\text{oxadiazole (III)} \xrightarrow[\text{agent}]{\text{acid binding}} I$$

(2)
$$R_1\text{-substituted acid halide (IV)} + HO-CH_2-\text{oxadiazole (V)} \xrightarrow[\text{agent}]{\text{acid binding}} I$$

(3)
$$R_1\text{-substituted acid (II)} + HO-CH_2-\text{oxadiazole (VI)} \xrightarrow[\text{water binding agent}]{-H_2O} I$$

(4)
$$R_1\text{-substituted ester (VI)} + HO-CH_2-\text{oxadiazole (V)} \xrightarrow{-ROH} I$$

In the formulae II to VI, the symbol $R_1$ has the meaning give for formula I, Z represents halogen, especially chlorine or bromine, and R represents $C_1$-$C_4$-alkyl, particularly methyl or ethyl.

Suitable acid-binding agents for the processes 1 and 2 are, in particular, tertiary amines such as trialkylamines and pyridine, also hydroxides, oxides, carbonates and bicarbonates of alkali metals and alkaline-earth metals, as well as alkali metal alcoholates such as potassiumt.butylate and sodium methylate. As water-binding agent for the process 3, there can be used, for example, dicyclohexylcarbodiimide. The processes 1 to 4 are performed at a reaction temperature of between $-10°$ and $100°$ C., usually between $20°$ and $80°$ C., at normal or elevated pressure and preferably in an inert solvent or diluent.

Suitable solvents or diluents are, for example, ethers and ethereal compounds such as diethyl ether, dipropyl ether, dioxane, dimethoxyethane and tetrahydrofuran; amides such as N,N-dialkylated carboxylic acid amides; aliphatic, aromatic as well as halogenated hydrocarbons, especially benzene, toluene, xylene, chloroform and chlorobenzene; nitriles such as acetonitrile; dimethylsulphoxide and ketones such as acetone and methyl ethyl ketone. The process 2 can also be performed in aqueous solution.

The starting materials of formulae II to VI are known or can be produced by methods analogous to known methods.

The compounds of formula I are present in different optically active isomers as well as cis/trans isomers. If therefore in the production process no pure optically active starting materials or cis- or trans-starting materials are used, then there are necessarily obtained diasteri-oisomers or cis/trans isomeric mixtures. The various stable isomeric mixtures can be separated, for example, by means of chromatographical separation methods into the isomeric forms, for example by adsorption on a separating material having selective adsorption activity, such as silica gel or aluminum oxide, and subsequent elution of the separated isomers with a suitable solvent, for example diethyl ether, hexane, methyl acetate or ethyl acetate. A further chromatographical separation method is gas chromatography. In certain cases, an isomeric mixture can be separated also by fractional distillation or fractional crystallisation.

It is understood that the present invention embraces both the separate stereoisomers or cis/trans isomers and the unseparated mixtures thereof.

The compounds of formula I are especially suitable for combatting insects of the family Muscidae. They have an unexpectedly better immediate and residual activity against *Musca domestica* as the chemically analogous compound of the formula

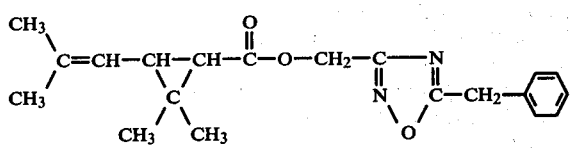

known from Chemical Abstracts 78, (1973) 72155 n.

The insecticidal action can be substantially broadened and adapted to suit given conditions by the addition of other insecticides and/or acaricides. Suitable additives are, for example, organic phosphorus compounds; nitrophenols and derivatives thereof; formamidines; ureas; other pyrethrin-like compounds; as well as carbamates and chlorinated hydrocarbons. Compounds of formula I are combined with particular advantage also with substances which have a synergistic or intensifying effect on pyrethroids. Examples of such compounds are, inter alia: piperonylbutoxide, propynyl ethers and propynyl phosphonates, 2-(3,4-methylenedioxyphenoxy)-3,6,9-trioxaundecane (Sesamex or Sesoxane), S,S,S-tributylphosphorotrithioates or 1,2-methylenedioxy-4-(2-(octylsulphonyl)-propyl)-benzene.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

Solid Preparations dusts, scattering agents, granulates (coated granulates, impregnated granulates and homogeneous granulates);

Liquid Preparations (a) water-dispersible active-substance concentrates: wettable powders, pastes or emulsions;
(b) solutions.

The content of active substance in the above described compositions is between 0.1 and 95%, in this connection it is to be mentioned that in the case of application from an airplane, or by means of other suitable devices, it is possible to use concentrations of up to 99.5% or even the pure active substance.

The active substances of formula I can be formulated for example as follows (parts denote parts by weight):

Dusts

The following substances are used in the preparation of (a) a 5% dust, and (b) a 2% dust:

(a)

5 parts of active substance,
95 parts of talcum;

(b)

2 parts of active substance,
1 part of highly dispersed silicic acid,
97 parts of talcum.

The active substances are mixed and ground with the carriers.

Granulate

The following substances are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Wettable powder

The following constituents are used to prepare (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid;

(b)

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in the appropriate mills and rollers. Wettable powders are obtained which can be diluted with water to give suspensions of the desired concentration.

Emulsifiable Concentrates

The following substances are used to produce (a) a 10%, (b) a 25%, and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)

25 parts of active substance,
2.5 parts of epoxidised vegetable oil,
10 parts of alkylarylsulphonate/fatty alcohol polyglycol ether mixture,
5 parts of dimethylformamide,
57.5 parts of xylene;

(c)

50 parts of active substance,
4.2 parts of tributylphenol-polyglycol ether,
5.8 parts of calcium-dodecylbenzenesulphonate,
20 parts of cyclohexanone,
20 parts of xylene.

It is possible to prepare from these concentrates, by dilution with water, emulsions of the desired concentration.

Spray

The following constituents are used to prepare (a) a 5% spray, and (b) a 95% spray:

(a)

5 parts of active substance,
1 part of epichlorohydrin,
94 parts of ligroin (boiling limits 160°–190° C.);

(b)

95 parts of active substance,
5 parts of epichlorohydrin.

The invention is further illustrated by the following Examples.

EXAMPLE 1

Production of 5-benzyl-1,2,4-oxadiazol-3-yl-methyl-2,2-dimethyl-3-(2,2-dichlorovinyl)-cyclopropanecarboxylic acid ester 8.36 g of 2,2-dimethyl-3-(2,2-dichlorovinyl)-cyclopropanecarboxylic acid, 8.35 g of 3-chloromethyl-5-benzyl-1,2,4-oxadiazole and 6.1 g of potassium carbonate (10% excess) are placed into 100 ml of methyl ethyl ketone and the whole is refluxed for 5 hours. The resulting suspension is thereupon fully concentrated by evaporation; the residue is taken up in 100 ml of toluene and washed with 30 ml of water. After drying of the crude product over sodium sulphate, separation by filtration and distillation, there is obtained the 5-benzyl-1,2,4-oxadiazol-3-methyl-2,2-dimethyl-3-(2,2-dichlorovinyl)-cyclopropanecarboxylic acid ester of the formula

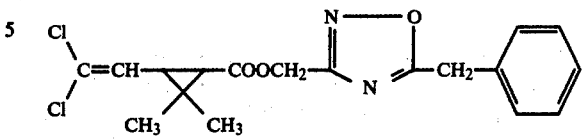

in the form of a yellow oil: $n_D^{20}$:1.5408.

The following compounds are produced in an analogous manner:

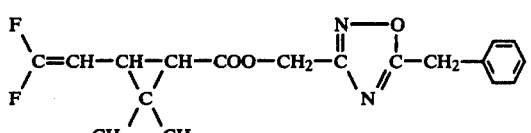

$n_D^{20} = 1.5082$

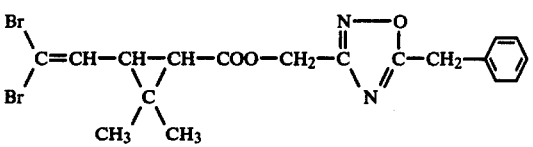

$n_D^{20} = 1.5635$

EXAMPLE 2

Comparison Test Against *Musca domestica*

Test compounds

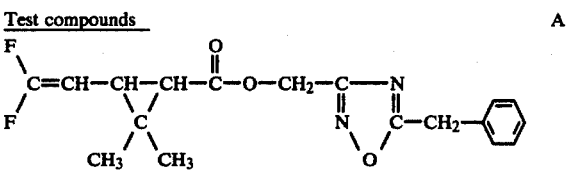

A

Claim 2

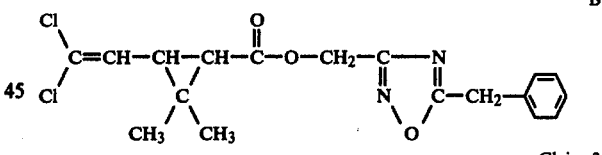

B

Claim 3

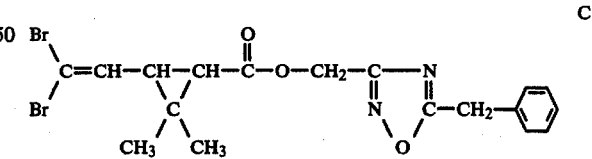

C

Claim 4

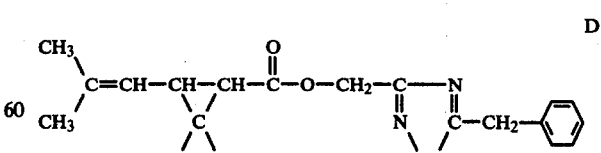

D

Chemical Abstract 78, (1973) 72155n.

Test-Solutions

Test-compounds dissolved in acetone; concentrations 5000, 1000, 100 and 10 ppm.

Test-Animal

*Musca domestica*

Test

Coatings of the acetonic solution of test substances were applied in Petri dishes (Diameter 9 cm), whereby concentrations of 5000, 1000, 100 and 10 ppm respectively of test substance per dish was used. 10 *Musca domestica* were placed in the dishes after one hour.

1. Control after 15', 30', 60', 2 hours, 4 hours and 8 hours on % mortality.
2. Control of the residual effect of the test-substances 8 days later using 10 new *Musca domestica*.

Test-Result

| Compound A | immediate activity in % of died *Musca domestica* | | | | | | residual activity (after 8 days) in % of died *Musca domestica* | | | | | |
|---|---|---|---|---|---|---|---|---|---|---|---|---|
| Conc. ppm | 15' | 30' | 60' | 120' | 240' | 480' | 15' | 30' | 60' | 120' | 240' | 480' |
| 5000 | 100 | — | — | — | — | — | 100 | — | — | — | — | — |
| 1000 | 100 | — | — | — | — | — | 100 | — | — | — | — | — |
| 100 | 90 | 90 | 95 | 100 | — | — | 30 | 70 | 80 | 90 | 95 | 95 |
| 10 | 5 | 40 | 55 | 75 | 80 | 80 | | | | | | |

| Compound B | immediate activity in % of died *Musca domestica* | | | | | | residual activity (after 8 days) in % of died *Musca domestica* | | | | | |
|---|---|---|---|---|---|---|---|---|---|---|---|---|
| Conc. ppm | 15' | 30' | 60' | 120' | 240' | 480' | 15' | 30' | 60' | 120' | 240' | 480' |
| 5000 | 100 | — | — | — | — | — | 100 | — | — | — | — | — |
| 1000 | 100 | — | — | — | — | — | 100 | — | — | — | — | — |
| 100 | 80 | 90 | 95 | 95 | 95 | 95 | | | | | | |
| 10 | 5 | 20 | 55 | 80 | 80 | 80 | | | | | | |

| Compound C | immediate activity in % of died *Musca domestica* | | | | | | residual activity (after 8 days) in % of died *Musca domestica* | | | | | |
|---|---|---|---|---|---|---|---|---|---|---|---|---|
| Conc. ppm | 15' | 30' | 60' | 120' | 240' | 480' | 15' | 30' | 60' | 120' | 240' | 480' |
| 5000 | 100 | — | — | — | — | — | 100 | — | — | — | — | — |
| 1000 | 100 | — | — | — | — | — | 100 | — | — | — | — | — |
| 100 | 90 | 100 | — | — | — | — | 75 | 90 | 100 | — | — | — |
| 10 | 35 | 50 | 90 | 95 | 95 | 95 | | | | | | |

| Compound D | immediate activity in % of died *Musca domestica* | | | | | | residual activity (after 8 days) in % of died *Musca domestica* | | | | | |
|---|---|---|---|---|---|---|---|---|---|---|---|---|
| Conc. ppm | 15' | 30' | 60' | 120' | 240' | 480' | 15' | 30' | 60' | 120' | 240' | 480' |
| 5000 | 80 | 100 | — | — | — | — | 0 | 0 | 0 | 5 | 15 | 75 |
| 1000 | 40 | 90 | 100 | — | — | — | 0 | 0 | 0 | 0 | 0 | 0 |
| 100 | 0 | 0 | 10 | 60 | 85 | 90 | | | | | | |
| 10 | 0 | 0 | 0 | 0 | 0 | 5 | | | | | | |

Conclusion

Compounds A, B and C have an excellent immediate and residual activity against *Musca domestica*, whereas compound D has a weak immediate and no residual activity against these insects.

We claim:

1. A 2,2-dimethyl-3-vinyl-cyclopropanecarboxylic acid ester of the formula

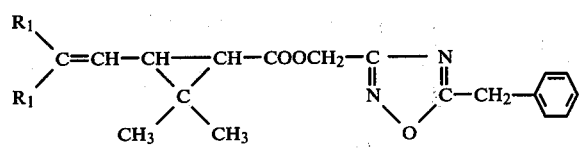

wherein $R_1$ represents fluorine, chlorine or bromine.

2. The compound according to claim 1 of the formula

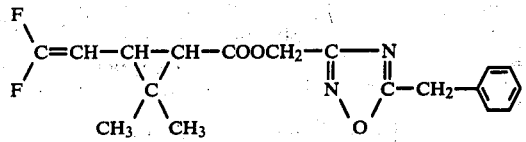

3. The compound according to claim 1 of the formula

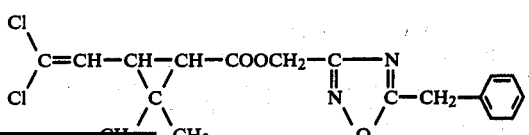

4. The compound according to claim 1 of the formula

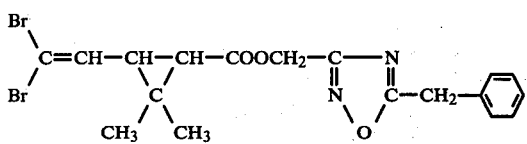

5. A insecticidal composition which comprises an insecticidally effective amount of a compound as claimed in claim 1 as active ingredient, together with a suitable carrier therefor.

6. A method of combatting insects of the family Muscidae at a locus, which method comprises applying to the locus an insecticidally effective amount of a compound as claimed in claim 1.

7. The method of claim 6, wherein said insect is *Musca domestica*.